(12) United States Patent
Taboas et al.

(10) Patent No.: US 8,709,793 B2
(45) Date of Patent: Apr. 29, 2014

(54) BIOREACTOR DEVICE, AND METHOD AND SYSTEM FOR FABRICATING TISSUES IN THE BIOREACTOR DEVICE

(75) Inventors: Juan M. Taboas, Washington, DC (US); Rocky S. Tuan, Bethesda, MD (US); Steven D. Hudson, Gaithersburg, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 1316 days.

(21) Appl. No.: 11/989,051

(22) PCT Filed: Jul. 20, 2006

(86) PCT No.: PCT/US2006/028417
§ 371 (c)(1),
(2), (4) Date: Apr. 23, 2009

(87) PCT Pub. No.: WO2007/012071
PCT Pub. Date: Jan. 25, 2007

(65) Prior Publication Data
US 2009/0215104 A1 Aug. 27, 2009

Related U.S. Application Data

(60) Provisional application No. 60/701,186, filed on Jul. 20, 2005.

(51) Int. Cl.
*C12M 1/00* (2006.01)
*C12M 1/34* (2006.01)
*C12M 1/36* (2006.01)
*C12M 1/38* (2006.01)
*C12M 3/00* (2006.01)
*C12N 5/00* (2006.01)
*C12N 5/02* (2006.01)

(52) U.S. Cl.
USPC .................. 435/288.7; 435/287.1; 435/283.1; 435/286.7; 435/325

(58) Field of Classification Search
USPC ........................................... 435/283.1–309.4
See application file for complete search history.

(56) References Cited

U.S. PATENT DOCUMENTS 4,945,896 A * 8/1990 Gade ............................. 600/202
5,994,091 A * 11/1999 Attridge et al. .............. 435/7.72
(Continued)

FOREIGN PATENT DOCUMENTS

WO    WO-03/087292    10/2003
WO    WO-2004/101743    11/2004
WO    WO 2005047466 A2 *    5/2005

*Primary Examiner* — Nathan Bowers
*Assistant Examiner* — Lydia Edwards
(74) *Attorney, Agent, or Firm* — Edwards Wildman Palmer LLP; Peter F. Corless

(57) ABSTRACT

A bioreactor device, and a method and system for fabricating tissues and growing cells and tissues in the bioreactor device, accommodates less than about 1 mL (or less than about 200 µL) of local medium volume but sample sizes of about 100 µL or greater. The bioreactor device includes a bioreactor chamber for containing a sample, where sample growth in response to mechanical, electrical, and biofactor stimulation is monitored through one or more optical ports. Embedded sensors are provided for measuring fluid pressure, pH, temperature, and oxygen tension. The bioreactor device can receive different types of mechanical loadings, including fluid shear, hydrostatic pressure, matrix compression, and clinorotation.

24 Claims, 11 Drawing Sheets

(56) References Cited

U.S. PATENT DOCUMENTS

| | | | |
|---|---|---|---|
| 6,074,610 A | 6/2000 | Huang et al. | |
| 6,653,124 B1 | 11/2003 | Freeman | |
| 6,964,738 B1 * | 11/2005 | Shen | 210/150 |
| 2002/0045911 A1 | 4/2002 | Fletcher et al. | |
| 2004/0195598 A1 * | 10/2004 | Tysoe et al. | 257/233 |
| 2004/0219659 A1 * | 11/2004 | Altman et al. | 435/284.1 |
| 2007/0042490 A1 * | 2/2007 | Welter et al. | 435/325 |

\* cited by examiner

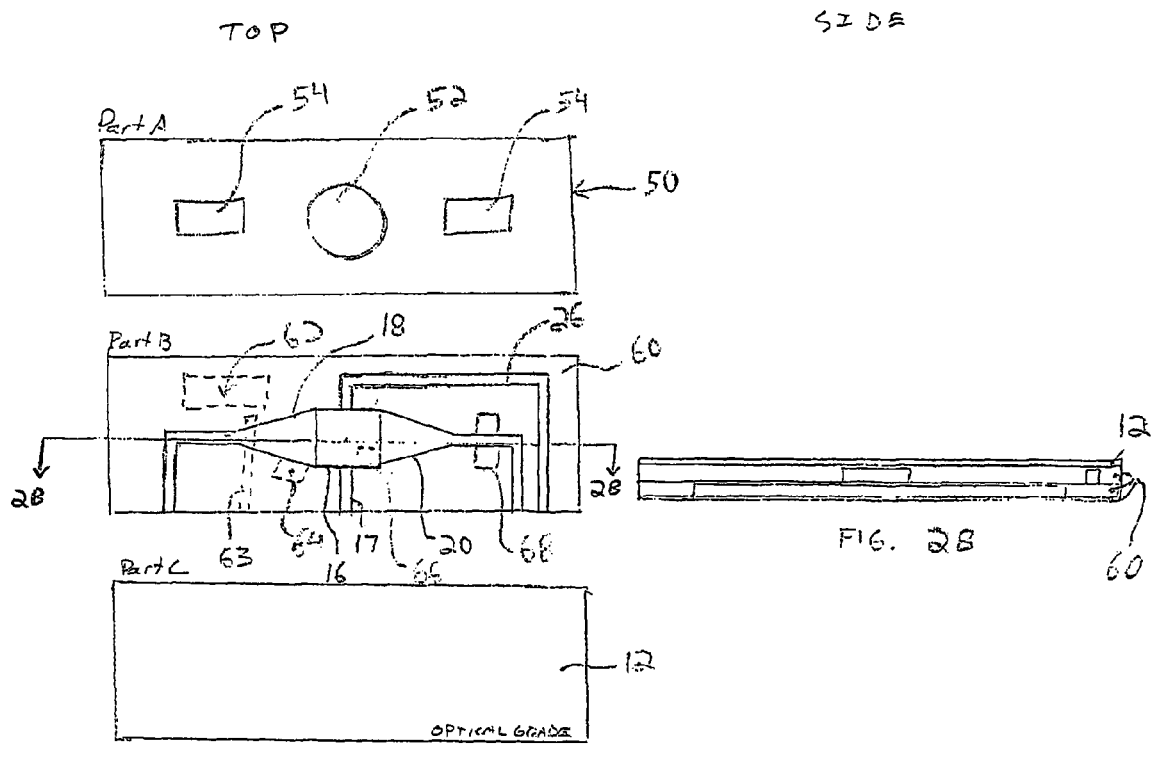
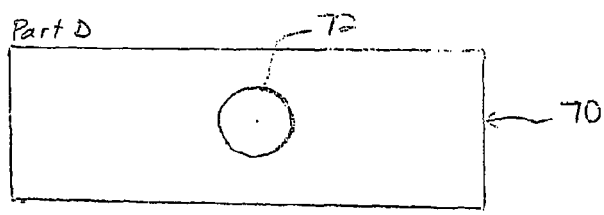

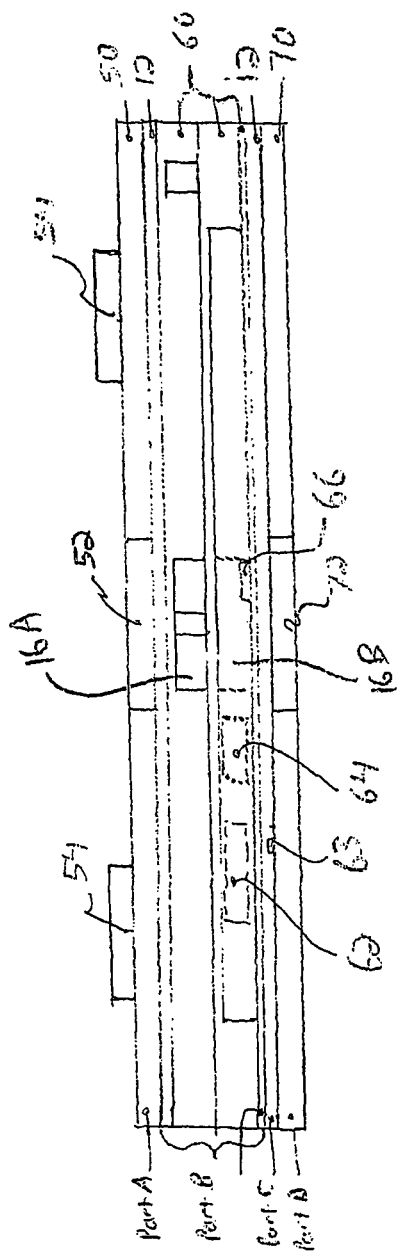

BIOREACTOR DEVICE, AND METHOD AND SYSTEM FOR FABRICATING TISSUES IN THE BIOREACTOR DEVICE

The present application claims the benefit of U.S. provisional application No. 60/701,186 filed Jul. 20, 2005, which is incorporated herein by reference in its entirety.

Research supporting this application was carried out by the United States of America as represented by the Secretary, Department of Health and Human Services.

FIELD OF INVENTION

The present invention relates to a bioreactor device, and methods and systems for growing and fabricating natural and engineered tissues in a bioreactor device, and more particularly relates to a bioreactor device on a millifluidic scale capable of delivering different mechanical and electrical loadings, controlling delivery of medium and biofactors, and non-invasively monitoring tissue growth.

BACKGROUND OF THE INVENTION

Bioreactors are commonly used to provide an environment for developing tissue constructs from samples including cells that grow to form tissue engineering constructs. Conventionally, to monitor the growth of cells in bioreactors, the cells or tissues are removed from the bioreactor and destructive assays performed.

Some bioreactors are designed to accommodate individual sample sizes of less than 1 µL, and are known as microfluidic systems. One example of a microfluidic system is disclosed in U.S. Pat. No. 6,653,124 to Freeman. In the Freeman patent, a plurality of microchambers are provided for cell culture, and each microchamber is in contact with one or more fluidic lines for supplying nutrients to the growing cells. The arrangement disclosed in Freeman is typical of microfluidic systems used to grow cells, but the microchambers are too small and cannot be used for growing natural or engineered tissues.

It would be desirable to provide a bioreactor device for accommodating larger sample sizes to facilitate growth of tissues in a bioreactor chamber while still maintaining a small volume of medium commonly used in microfluidic systems. It would also be desirable to provide a bioreactor system that can flexibly accommodate different types of mechanical loading, deliver biofactors, and monitor tissue growth in a non-invasive manner.

SUMMARY OF THE INVENTION

A bioreactor device, and a bioreactor system and method for culturing cells and growing and fabricating natural and engineered tissues in the bioreactor device are disclosed. The system includes at least the bioreactor device and a fluid circuit for controlling medium flow through the bioreactor device. Preferably the system is "millifluidic," i.e., capable of accommodating sample sizes of cells and/or tissues that are larger than those accommodated in microfluidic systems, preferably greater than about 100 µL, but local medium volumes (within the vicinity of the sample) that are relatively small, e.g., less than twice the sample volume. An advantage of the millifluidic system of the subject invention is the ability to grow larger tissue samples than microfluidic systems, while containing a preferred total medium volume of less than about 2 mL, which is significantly smaller than medium volumes utilized in commercial systems, which often contain medium volumes greater than about 1 L. As used herein, the term "local medium volume" refers to medium located in the bioreactor chamber and connecting channels, whereas the term "total medium volume" refers to medium provided throughout the system, including that provided in the bioreactor device and the fluid circuit.

Monitoring of sample growth and function in response to biofactor, electrical, and mechanical stimulation is provided via embedded sensors and spectroscopy and microscopy measurements taken through one or more optical ports in the bioreactor device. Embedded sensors are provided for measuring one or more of fluid pressure, pH, temperature, impedance, and oxygen tension.

The bioreactor device of the subject invention can flexibly accommodate a plurality of different types of mechanical and electrical loadings or stimulation, including but not limited to fluid shear, hydrostatic pressure, matrix compression, and clinorotation (net microgravity). The system of the subject invention can be a closed-loop system that allows controlled delivery of medium and biofactors, where the biofactors are maintained in a suitable concentration because the medium volume is generally low compared to conventional bioreactor systems.

The bioreactor device includes at least one bioreactor chamber containing a sample, where the bioreactor chamber can include one or more levels, preferably at least an upper level and a lower level. The sample can be housed in the lower level(s), where the uppermost level is used to facilitate mechanical stimulation, e.g., by matrix compression. The lower levels of the bioreactor chamber or a single lower level thereof preferably are fluidly coupled to the fluid circuit so that medium and/or biofactors can be controllably delivered to the sample contained in the bioreactor chamber. Levels of the sample are exposed to different fluids and/or biofactors via discrete fluid circuits coupled to the chamber levels.

The bioreactor device of the subject invention can accommodate a plurality of sample types including tissue explants, engineered tissues, and cells cultured on 2-dimensional (2D) surfaces (planar culture) and on non-planar surfaces such as 3-dimensional (3D) scaffolds.

Other aspects and embodiments of the invention are discussed below.

BRIEF DESCRIPTION OF THE DRAWINGS

For a fuller understanding of the nature and desired objects of the present invention, reference is made to the following detailed description taken in conjunction with the accompanying drawing figures wherein like reference character denote corresponding parts throughout the several views and wherein:

FIG. 2A is an exploded parts view of the bioreactor device of FIG. 1, and further including various sensors for use with the subject invention;

FIG. 2B is a cross-sectional side view of the bioreactor device through line 2B-2B in FIG. 2A;

FIG. 3A is an enlarged cross-sectional side view of the bioreactor device of FIG. 2A in an assembled condition;

DESCRIPTION OF THE PREFERRED EMBODIMENT(S)

Figure 1A:
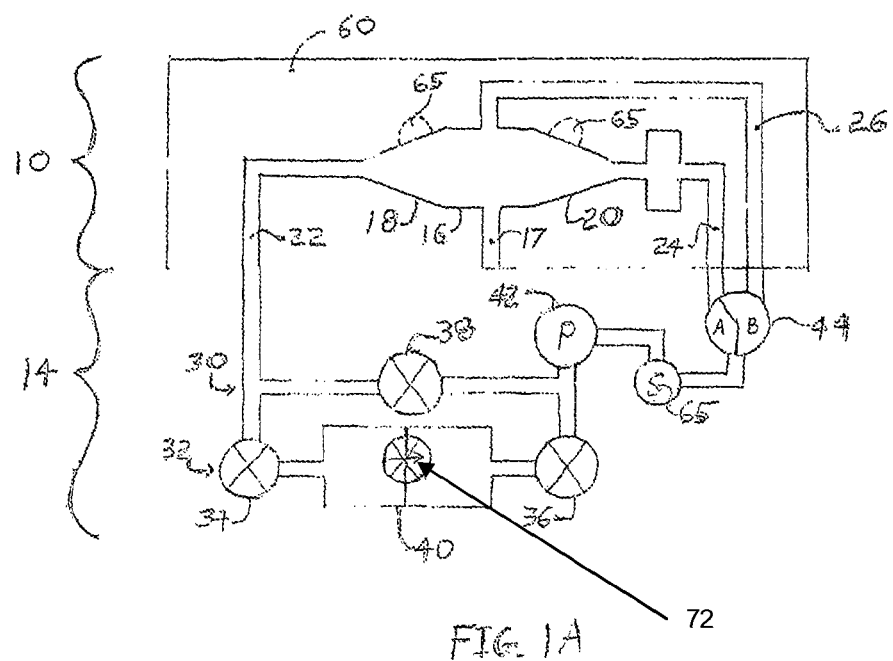
FIG. 1A is a schematic plan view of a bioreactor system including the bioreactor device and a fluid circuit for controlling medium flow through the bioreactor device, according to the subject invention.

Referring now to the various figures of the drawing wherein like reference characters refer to like parts, there is shown in FIG. 1A a bioreactor system including a bioreactor device connected to a fluid circuit for controlling medium flow through the bioreactor device. The bioreactor device can be used to grow and fabricate natural and engineered tissues, in which sample tissue volumes preferably are greater than about 10 µL (microliters), more preferably greater than about 100 µL. Local medium volumes surrounding the sample in the bioreactor chamber can be less than about 1 mL, more preferably less than about 200 µL. Total medium volumes, including medium contained in the reservoir, can be less than about 2 mL, although larger or smaller sample sizes or medium volumes can be used.

The bioreactor device of the subject invention is adapted to contain tissue volumes on a milliliter scale, and thus can be referred to as a "millifluidic system," as distinguished from prior art microfluidic systems in which individual sample volumes generally are on the order of 1 µL. An advantage of the millifluidic system of the subject invention is the ability to grow larger tissue samples, as compared to microfluidic bioreactor systems, which have smaller sample areas and generally are configured to grow samples on a cellular level. At the same time, the bioreactor system of the subject invention can contain approximately the same or smaller total medium volumes than microfluidic systems, and significantly smaller total medium volumes than commercially available bioreactor systems, which often contain fluid (medium) volumes of at least 1 L.

A method and system for fabricating tissue samples in the bioreactor device can involve the culture and analysis of three-dimensional biologics, for example, mammalian cells, engineered tissues such as multiphasic tissues and organoids, and tissue explants or biopsies. Tissue samples can be provided as natural or engineered tissues in the bioreactor device. Cells can be cultured on two-dimensional surfaces and three-dimensional scaffolds.

The bioreactor device of the subject invention can flexibly accommodate a plurality of different types of mechanical and electrical loadings or stimulation, including but not limited to fluid shear, hydrostatic pressure, matrix compression, and clinorotation (net microgravity). Prior art bioreactors do not have the same capability to deliver a plurality of types of mechanical stimulation nor the capability to simultaneously deliver a plurality of types of mechanical and electrical stimulation. Simultaneous clinorotation of multiple chambers in the bioreactor device can be performed via rotation along an axis through the chambers.

Delivery of medium is achieved in the bioreactor device via periodic and/or continuous perfusion of nutrients to maintain growth and viability of tissue samples. The bioreactor device is also used to deliver biofactors for sample stimulation, including growth factors and cytokines. According to the subject invention, a closed-loop fluid system is provided that maintains a sterile environment (free of microorganism infection) and allows controlled delivery of medium and biofactors. Because the system preferably is closed loop, biofactors can be recirculated and concentrated. Because the system of the subject invention is millifluidic, the medium level is sufficiently small to prevent endogenous biofactors produced by the sample from becoming unsuitably diluted in medium, and smaller amounts of exogenous biofactors delivered by the user are required for a given concentration in solution. However, unlike microfluidic systems, the millifluidic system of the subject invention is capable of growing tissues, in addition to individual cells. Therefore, tissue constructs can be fabricated, and tissue constructs and organisms grown according to the subject invention.

For example, an application of the bioreactor device is to culture embryos, and study growth over time using the in situ monitoring capabilities of the subject invention, as described herein. Common embryo models include the chicken and frog. For example, chick embryos placed within a hydrogel can be grown in the bioreactor device. Tissue sample sizes range from about 10 µL to about 1 µL, although larger or smaller sample sizes can be used.

The system and method of the subject invention allow non-invasive monitoring of tissue growth in the bioreactor device. Monitoring of biologic (sample) growth, response, and function to biofactors, electrical, and mechanical stimulation can be provided via embedded sensors and 2-dimensional (2D) and 3-dimensional (3D) spectroscopy and microscopy through one or more optical ports provided in the bioreactor device, For example, spectroscopy measurements can be obtained through absorbance and emission from dyes and reporters using external devices such as a microplate reader. Microscopy readings can be measured using techniques such as Confocal Laser Scanning Microscopy and Coherent Anti-strokes Ranian Scattering. Embedded sensors can be used to measure system parameters such as fluid pressure, pH, temperature, impedance, and oxygen tension (for example, via fluorescence quenching of dye-covered glass). For example, pH can be measured through one or more ISFET sensors. According to the subject invention, monitoring can occur in real time and under computer control.

Figure 1B:
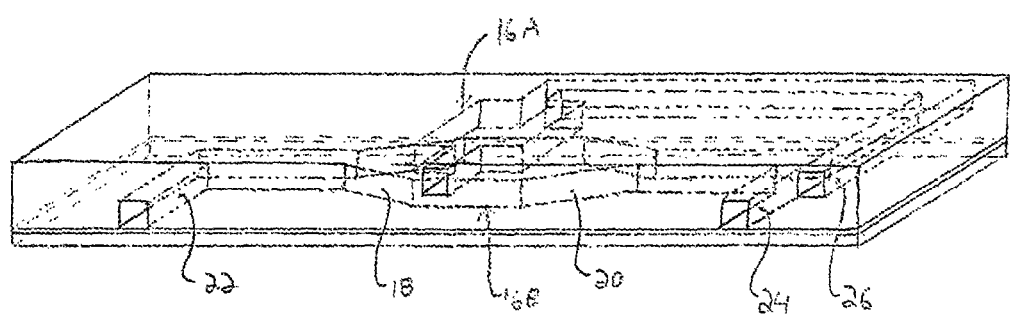
FIG. 1B is a perspective view of the bioreactor device of FIG. 1A showing two levels of fluid pathways.

Referring to FIG. 1A, a bioreactor device 10 preferably includes various components mounted on a plate 12 (see FIG. 1B), where the bioreactor device 10 is connected to a fluid circuit 14. The fluid circuit 14 includes flow paths arranged inside the bioreactor device, and one or more valves and other parts external to the bioreactor device. Fluid flow can be unidirectional or bidirectional (including reciprocating), and automatically controlled by preprogrammed instructions, e.g., through a microchip or computer, including appropriate hardware and/or software. Preferably, fluid is capable of being circulated in a bidirectional manner through the bioreactor device.

The bioreactor device 10 includes at least one bioreactor sample chamber 16 arranged on the plate 12, which is preferably a glass plate or slide, and encapsulated in a housing having a plurality of fluid channels, preferably a silicone housing. The bioreactor chamber includes one or more levels; for example, the bioreactor chamber 16 can include an upper level 16A and a lower level 16B (see FIGS. 1B and 3A). The lower level preferably is configured for receiving and delivering fluid (medium) to a sample contained in the chamber. For example, the lower level can be used for controlled delivery of biofactors and fluid shear. Multiple lower levels facilitate the production and growth of multiphasic tissues. The upper level of the bioreactor chamber 16 can be filled with fluid under pressure for providing matrix compression according to the subject invention. Alternatively, other types of mechanical stimulation can be delivered through the upper and/or lower levels. A plurality of chamber levels can be employed, each individually coupled to discrete fluid circuits.

Figure 3B:
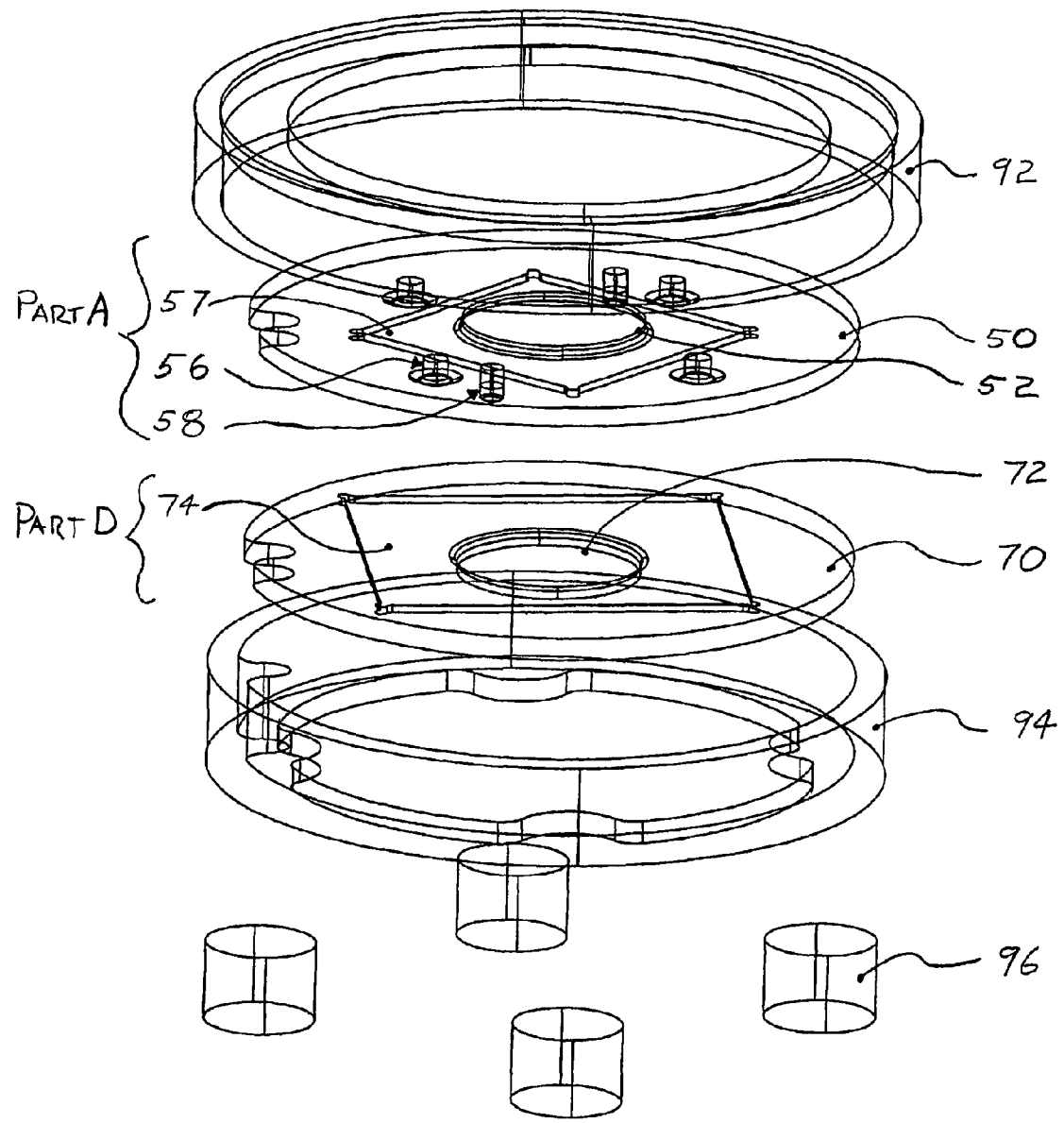
FIG. 3B is a perspective exploded parts view of the bioreactor device of FIG. 2A shaped for enclosure within a cylindrical housing.
Figure 3C:
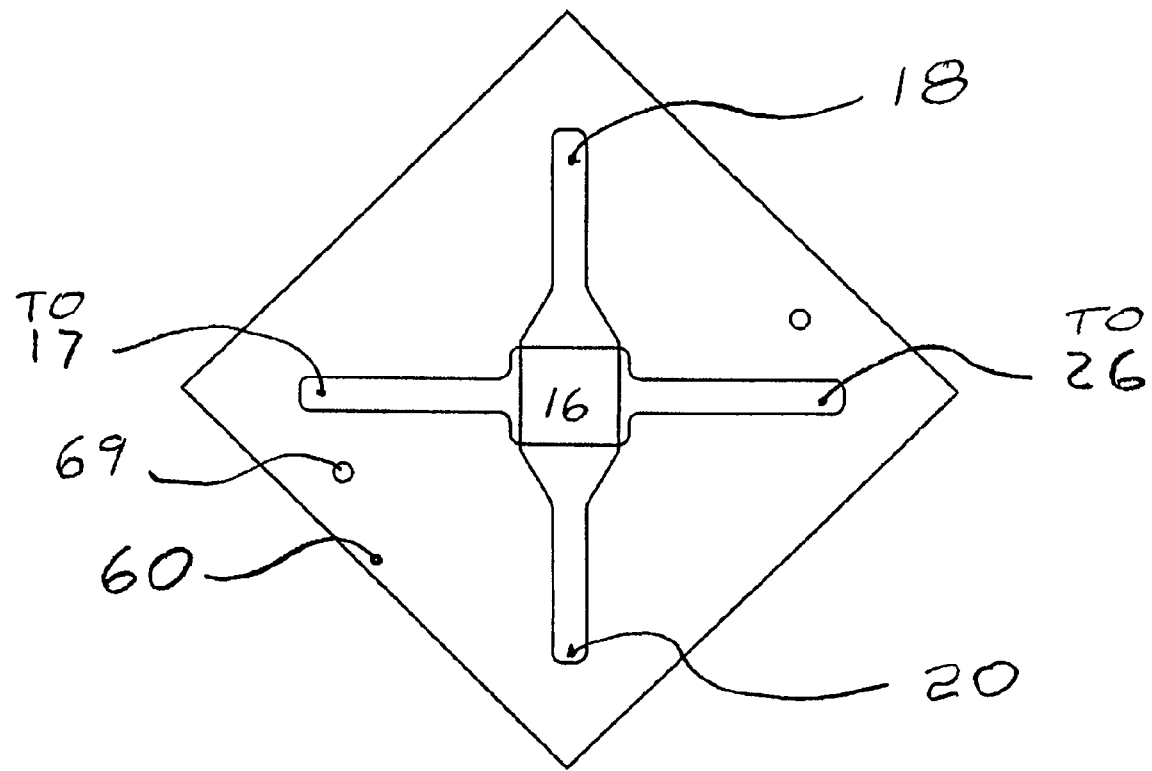
FIG. 3C is a top view of the bioreactor device of FIG. 3B showing two levels of fluid pathways in a generally perpendicular pattern.
Figure 4:
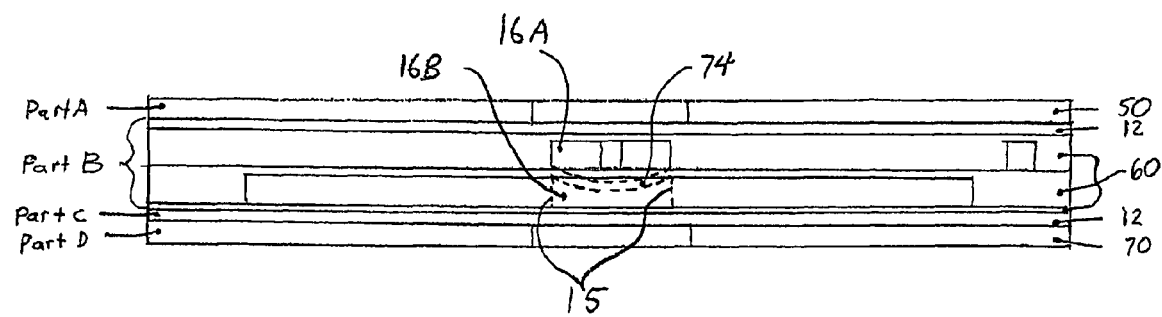
FIG. 4 is a cross-sectional side view of the bioreactor device of FIG. 3A during matrix compressive loading of a sample, where deflection of a membrane has been magnified (not drawn to scale)

Referring to FIGS. 1-4, in a preferred embodiment, the lower level 16B of the bioreactor chamber 16 is fluidly coupled to the fluid circuit 14 by flow channels 18 and 20. The flow channels 18 and 20 are fluidly connected to pipes 22 and 24, respectively, the pipes capable of exchanging fluid (medium) via the fluid circuit 14. An additional pipe 26 is connected to flow channels in the upper level 16A of the bioreactor chamber 16, and can be used for matrix compression. Referring to FIG. 4, filters 15 on opposite ends of the chamber 16 can be employed to contain the sample.

As shown in FIG. 1A, the fluid circuit 14 includes a plurality of components for controlling delivery of fluid (medium), biofactors (e.g., growth factors and cytokines), and mechanical stimulation to a sample contained in the bioreactor chamber 16. The valves can be opened or closed, and a pump controlled to determine whether fluid is allowed to circulate through the bioreactor device, or whether new fluid is pumped through the bioreactor chamber. The arrangement depicted in FIG. 1A is exemplary, and a different arrangement can be provided with one or more of the components of FIG. 1A, or additional components, according to specific requirements of the bioreactor device.

Referring to FIG. 1A, in the fluid circuit 14, fluid can be circulated or recirculated through one or more generally parallel pathways. In FIG. 1A, two fluid pathways 30 and 32 are depicted, and fluid flow is directed through one or both of these pathways depending on the operation to be performed in the bioreactor device. The fluid circuit 14 includes first and second valves 34 and 36 arranged in the second pathway 32, and a third valve 38 arranged along the first pathway 30. Preferably the valves 34, 36, and 38 are automatic valves that are configured to open or close based on a preprogrammed sequence, e.g., under computer control, but manual valves can be substituted for the automatic valves and controlled manually by an operator.

A fluid reservoir 40 preferably is provided between the first and second valves 34 and 36. Fresh medium and/or biofactors can be contained in the fluid reservoir 40, where delivery of the medium is either manually or automatically controlled. A pump 42 is arranged downstream of the first and second pathways 30 and 32, where the "downstream" direction refers to a left to right movement of fluid in FIG. 1A, but where fluid can move in the opposite direction or in a bidirectional manner. The pump 42 preferably is a peristaltic pump capable of maintaining the pumped fluid/medium in a sterile condition, and preferably having a dynamic loading range.

The fluid reservoir preferably contains a septum that separates the fluid into multiple compartments, preferably two compartments, and serves as a multifunction valve regulating flow direction and fluid mixing. The septum can be used to permit bidirectional fluid flow and diffusion between both compartments, restrict fluid flow and diffusion to one direction (e.g., downstream), and inhibit fluid flow and diffusion between compartments. A unidirectional flow septum and an open septum provide for both continuous (static) and cyclic (dynamic) unidirectional perfusion and reciprocating perfusion, while a closed septum provides for reciprocating perfusion. During reciprocating flow stimulation of the sample in the bioreactor chamber, the valve 38 can be opened and the valves 34 and 36 closed to provide positive pressure head as the driving force for perfusion in both directions. Fresh medium and biofactors may be delivered from the right reservoir compartments and sampled downstream in the left reservoir compartment, for example, using the closed septum or unidirectional septum. The fluid reservoir may be open to the atmosphere or sealed depending on the desired mode of operation. A sealed reservoir is preferred for use during clinorotation mechanical stimulation. Diffusion of gases to and from the medium during sealed reservoir operation is provided through the fluid circuit 14 tubing and encapsulant 60 (see FIG. 1A). Gaseous diffusion is enhanced in the medium in the open reservoir. As a further option, the medium in the reservoir may be aerated.

Downstream of the pump 42 is a valve 44, either a manual or automatic valve, which enables a fluid connection to one of multiple levels in the bioreactor chamber 16. For example, in FIG. 1A, the valve 44 preferably is a manual valve with connections labeled "A" and "B" corresponding to upper and lower levels of the bioreactor chamber 16, respectively.

An exemplary structure of the bioreactor device 10 will be described with reference to FIGS. 1 to 3. The assembled bioreactor device 10 shown in FIG. 1A includes a plurality of layers (see Parts A, B, C, and D in FIG. 2A). A top layer 50, also labeled "Part A," includes an optical port 52 preferably centered over the bioreactor chamber 16 to allow imaging of a sample contained in the bioreactor chamber 16. Similarly, a bottom layer 70, also labeled "Part D," includes an optical port 72 preferably centered under the chamber 16. Removal of Part D (the bottom plate 70) and Part C (the lower plate 12) provides easy access to the sample contained in the bioreactor chamber 16, where the lower plate 12 preferably forms a pressure tight seal with Part B. A thin sheet of silicone or like material can be incorporated into the lower plate 12 to form a seal with the Part B.

As shown in FIG. 2A, the middle layers (labeled Parts B and C) include components of the bioreactor device 10 shown in FIG. 1A. For example, Part B includes various components, preferably encapsulated by an encapsulant 60 made of silicone or a similar biocompatible material, that are mounted on the lower plate 12 ("Part C"), where the lower plate 12 preferably is made of optical grade glass. Optionally, a layer of encapsulant 60 can be provided between the bioreactor chamber 16 and the lower plate 12 (see FIG. 3A) as a component of Part C. As a further option, an upper glass plate 12 can be included between the top layer 50 and the encapsulant 60 of "Part B," as shown in FIGS. 2A and 3A.

When Parts A through D are combined, the encapsulant 60 contacts the lower and/or upper plates 12, the plates being capable of maintaining the various components in a generally flat condition sandwiched between the top and bottom plates 50 and 70, which if desired may be made out of a thermally or electrically conductive material. Part C, the lower plate 12, and Part B combine to form a pressure tight seal. When the lower face of Part B and Part C are treated with reactive oxygen (oxygen plasma), the seal strength of Part B with the lower glass slide 12 (Part C) is enhanced. When the encapsulant 60 is combined with the lower glass plate 12 (Part C), the pressure seal is created between the encapsulant of Part B and Part C, plate 12. In order to prevent leakage of high pressurized fluid between the encapsulant material of Part B and Part C, the silicone encapsulant 60 can be partially cured or plasma treated before combining. After curing of the encapsulant 60, the bioreactor chamber 16 is accessed using a syringe through the encapsulant, e.g., to inject cells or take samples as desired.

The various components encapsulated in the encapsulant 60 of "Part B" include one or more temperature sensors, such as an integrated circuit (IC) temperature sensor 62 shown in FIGS. 2A and 3A. The temperature sensor 62 can be arranged in any desired position on or near the bioreactor chamber 16, preferably proximate to one of the flow channels 18, 20 either upstream or downstream of the sample contained in the bioreactor chamber.

The various mechanical and electrical components of the bioreactor system are preferably miniature components that minimize total bioreactor size and make the entire bioreactor system self-contained, thus providing for a small foot print for the device, for portability, and for continued bioreactor operation during clinorotation. For example, the bioreactor system may be powered during normal operation with an external two-lead power supply while during clinorotation with a battery mounted with the bioreactor system. The various mechanical and sensor components of the bioreactor system, including the pressure sensors 65, temperature sensor 62, ISFETS sensors 64, pump 42, valves (34, 36, and 38), and heaters 54, are preferably controlled using microchip devices. The pump 42 is preferably a mini-peristaltic pump. The valves are preferably mini-pinch valves than restrict flow through tubing. Sensor data is preferably stored in microchip memory and later downloaded to a computer for analysis and logging.

The bioreactor device with Parts A through D, as shown in FIGS. 2A and 3A, preferably are shaped to fit within a cylindrical enclosure composed of enclosure elements 92 and 94, and a plurality of legs 96, as shown in FIG. 3B. In this configuration, Part A or layer 50 includes an optical port 52, one or more fluid ports 56, a plurality of alignment pins 58, and a recessed plate holder 57. The fluid ports 56 form a connection between the external fluid pipes (reference numbers 17, 22, 24, and 26; see FIG. 1A) and internal fluid channels (reference numbers 18 and 20; see FIGS. 1A, 2A, and 3C). A recess 57 preferably is configured to receive a plate 12 (see FIGS. 2B and 3A). The alignment pins 58 can be used to guide the fitting of fluid channels in Part B onto the fluid ports 56 in Part A. In the depicted cylindrical configuration, Part D refers to layer 70 with the optical port 72 and a recessed plate holder 74. A recess 57 preferably is configured to receive Part C (see FIGS. 2A and 3A). In certain embodiments, the orientation of Parts A through D can be flipped within the enclosure elements 92 and 94. A plurality of detachable legs 96 preferably are configured to elevate the enclosure element 94 and provide space for fluid pipes to exit Part A when Parts A through D are flipped in orientation. By rotating the enclosure element 92 and the detachable legs 96 on their threaded axis it is possible to seal the ports 56 in Part A with the fluid channels in Part B (channels 17, 18, 20, and 26; see FIGS. 1A, 2A, and 3C) and tightens Part B together with Part C, which can be used to close access to the sample chamber 16 and enhance the pressure seal between Parts B and C. For the cylindrical enclosure, the fluid channels in Part B preferably are oriented in a perpendicular manner (see FIG. 3C). Part B in FIG. 3C can include a plurality of alignment holes in the encapsulant 60 which match with the alignment pins 58 in Part A (see FIG. 3B).

Referring to FIGS. 2A and 2B, a partial cross-sectional view of the bioreactor device is shown through "Part B" along the cross-section 2B-2B illustrating the bioreactor chamber 16 encapsulated by the encapsulant 60. As shown in FIG. 2B, the encapsulant made of silicone or like material preferably surrounds upper and lower levels of the bioreactor chamber 16.

Placement of a sample in the bioreactor chamber 16 will be described with reference to FIGS. 2A, 3A, and 3B. A first step involves seeding cells, placing tissue(s), or casting one or more gels as a sample in the bioreactor chamber 16. Cells may also be seeded on Part C over the area in contact with the bioreactor chamber. Preferably, in a multilevel bioreactor chamber such as that shown in FIG. 3A, the sample is prepared in the lower level 16B. Next, a second step involves filling the flow channels 18 and 20 with medium, e.g., by injecting fluid (medium) into the flow channels 18 and 20. Subsequently, in a third step, the middle layers (Parts B and C) of the bioreactor device are assembled, such that the bioreactor chamber 16 and other components are supported on the lower plate 12. A fourth step involves assembling the upper and lower plates (Parts A and D) to the assembled middle layers, and clamping together the bioreactor device. The device is preferably clamped together using a cylindrical enclosure composed of the elements 92 and 94 (see FIG. 3B). A fifth step involves connecting the fluid reservoir 40 to the pipes 22 and 24 (see FIG. 1), followed by bleeding medium through these pipes (sixth step). With the cylindrical enclosure of FIG. 3B, pipes 22 and 24 are preferably connected to Part A and the reservoir 40 prior to clamping the device together. The upper level of the chamber 16 is bled through a fluid channel and a pipe 17.

After the sample has been loaded in the bioreactor chamber 16, it may be desirable to exchange medium using the fluid circuit 14 as described with reference to FIG. 1A. For example, the third valve 38 is closed, and the first and second valves 34 and 36 are opened, so that fluid (medium) can be pumped from the reservoir 40 through the fluid circuit. In fact, the reservoir 40 can be used to controllably deliver various fluids to the bioreactor chamber, including but not limited to: glucose, biofactors, and various types of media. Fluids in the reservoir 40 can be released at preprogrammed intervals under computer control.

Controlled delivery of biofactors can be made through the reservoir 40; alternatively, biofactors can be injected directly into the bioreactor chamber 16 containing the sample. A further alternative for delivery of biofactors involves use of a separate pre-chamber known as a biofactor delivery chamber 68 (see FIG. 2A). The biofactor delivery chamber 68 is particularly useful when a gel doped with the biofactor is cast as the biofactor carrier in the delivery chamber 68 or when another such carrier such as a scaffold loaded with biofactors or cells is placed as a carrier within the delivery chamber 68, and biofactors preferably are slowly released over time as the biofactors diffuse from the carrier or are released as the carrier degrades. Delivery of biofactors contained in the biofactor delivery chamber 68 to the sample in chamber 16 can be controlled in a predesigned manner by the type and design of the carrier. Delivery of biofactors from the biofactor delivery chamber 68 can further be controlled by modulating the medium flow through fluid channel 20. For example, a bolus of biofactor can be delivered to the sample in chamber 16 by pumping the fluid near the biofactor delivery chamber 68 to the sample chamber 16.

Various operations that can be performed on a sample contained in the bioreactor chamber 16 will be discussed with reference to the fluid circuit 14 of FIG. 1A. According to the subject invention, samples contained in the bioreactor chamber 16 can be subjected to perfusion, hydrostatic pressure, fluid shear, compression, electrical stimulation, monitoring of pH and oxygen levels, testing of mechanical properties, and in situ imaging, among other monitoring functions, where one or more of these activities can be carried out simultaneously.

To stimulate a sample contained in the bioreactor chamber using hydrostatic pressure, the first and third valves 34 and 38 are closed, effectively restricting circulation of fluid through the bioreactor chamber, and the pump 42 activated to apply a positive pressure head on the pipe 24. The pump can be activated to apply static and dynamic pressure waveforms. To apply unidirectional fluid shear, the valve 38 is closed, the valves 34 and 36 opened, and the pump 42 activated to apply a positive pressure head on the pipe 24. Alternatively, to apply either unidirectional or reciprocating fluid shear, the first and second valves 34 and 36 are closed, while the third valve 38 remains open, thereby causing fluid to travel through the first pathway 30 of the fluid circuit 14. The pump 42 is activated to apply a positive pressure head on the pipes 22 or 24 by reversing the pump rotation. As a further alternative, to permit medium exchange, whereby fluid (medium) contained in the reservoir 40 is circulated through the bioreactor device, the third valve 38 is closed, while the first and second valves 34 and 36 remain open, thereby pumping fluid (medium) through the second pathway 32 of the fluid circuit. During application of each of the above types of mechanical stimulation, the manual valve 44 remains in position "A" such that any fluid circulation occurs through the lower level of the bioreactor chamber.

To provide matrix compression, the manual valve 44 is switched from setting "A" to setting "B", valves 34 and 36 opened, and the third valve 38 is closed, allowing fluid (medium) to flow into the upper level of the bioreactor chamber, causing deflection of a membrane 74 shown in FIG. 4. The membrane 74 may also be deflected up or down with the use of an external plunger connected through the top optical port 52, thus applying tensile or compressive forces to the sample (see FIG. 2A).

Figure 6A:
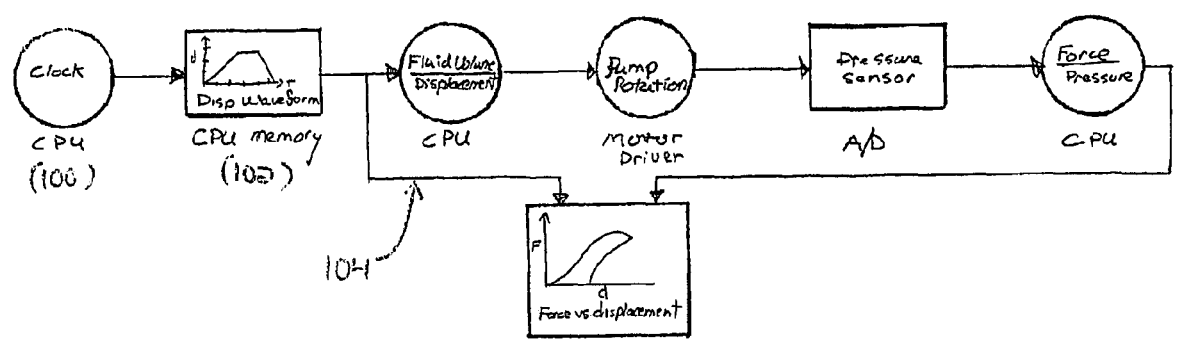
FIG. 6A is a flowchart of a method for controlled displacement testing (e.g., stress relaxation test) of a sample within the bioreactor chamber.
Figure 6B:
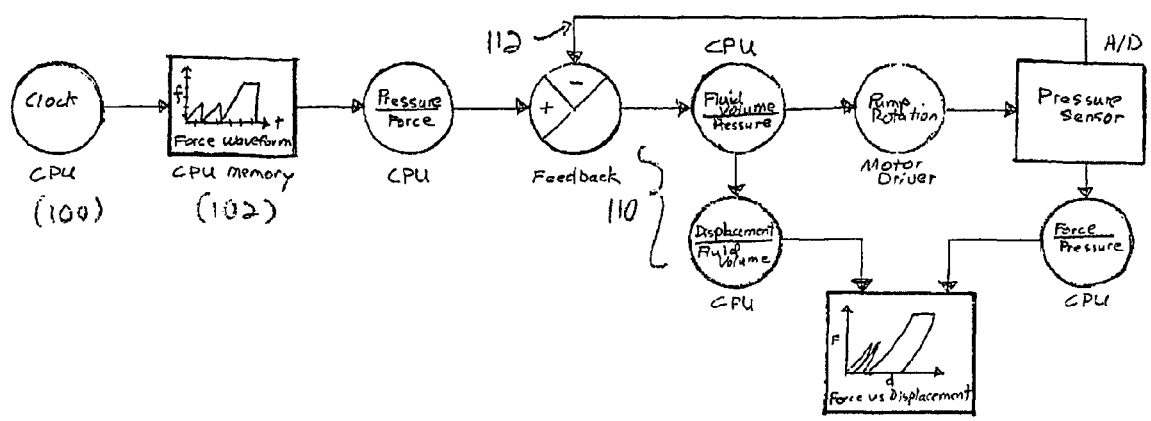
FIG. 6B is a flowchart of a method for controlled force testing (e.g., creep test) of a sample within the bioreactor chamber.
Figure 6C:
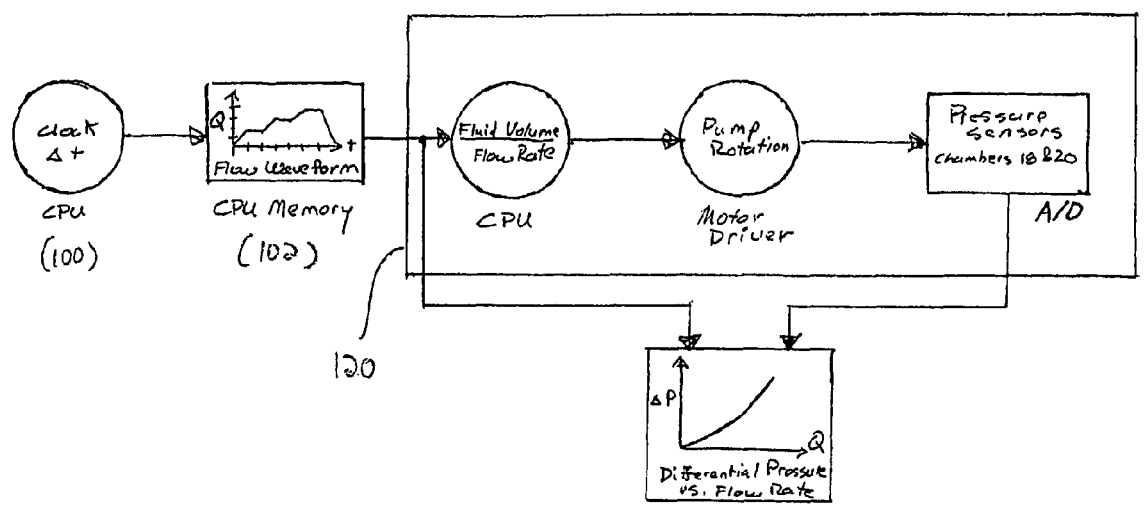
FIG. 6C is a flowchart of a method for permeability testing of a sample within the bioreactor chamber.
Figure 6D:
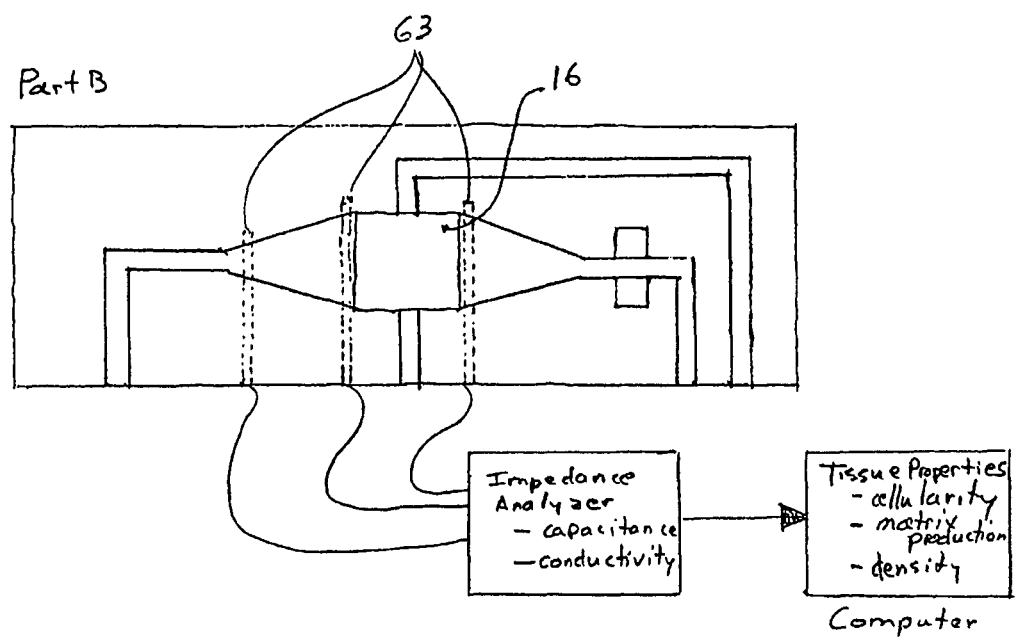
FIG. 6D is a schematic diagram of bioreactor electrical connections for impedance testing of a sample within the bioreactor chamber.

To provide electrical stimulation of the sample, controlled electric fields are applied through the embedded electrodes 63 (see FIG. 6D).

The bottom layer 70 includes an optical port 72 preferably centered over the bioreactor chamber 16 and aligned with the optical port 52 of the top layer 50 (see FIG. 3A); alternatively, one or more of the optical ports 52 and 72 can be omitted. Imaging measurements using spectroscopy or microscopy can be made through respective optical ports 52 and 72 in the top and/or bottom layers 50 or 70 (see FIG. 5). Preferably optical measurements include images obtained with lenses having numerical apertures up to about 1.3.

The top layer 50 also can include one or more heating elements 54, preferably a MOSFET (metal oxide semiconductor field-effect transistor) operating in the forward regime or the like, for heating the top and/or bottom layers of the bioreactor device to maintain the sample chamber 16 at a predetermined temperature (see FIGS. 2A and 3A). Heating elements may also be incorporated directly into the plate 12, for example, via glass laminated with indium-tin oxide. For example, it may be desirable to maintain a predetermined temperature in the bioreactor device in order to obtain time-lapse microscopy measurements of a sample. Imaging can be carried out using techniques such as Confocal Laser Scanning Microscopy and Coherent Anti-strokes Raman Scattering. Further, measurements can be taken through the one or more optical ports using a spectrophotometer, a microplate reader, or other known devices.

One or more pH sensors 64 can be provided in the bioreactor device, either on or near the bioreactor chamber 16 or flow channels 18, 20. Preferably the pH sensors are ISFET (ion-sensitive field effect transistor) sensors that are referenced to a reference electrode 63. The reference electrode 63 can be a chemical reference electrode (e.g., KCl) or in a preferred embodiment, the reference electrode 63 is plated silver received on the lower glass plate 12. Measurements from the pH sensors preferably are taken at discrete intervals, e.g., under computer control. According to the subject invention, the temperature and ISFET pH sensors provided in the bioreactor device can be read in real time through the electronic output of these sensors, preferably using data acquisition software. The sensors 64 can include ISFET sensitive to various ionic species including hydronium, sodium, calcium, and potassium. In one embodiment, the pH sensor can be a doped membrane that is read through one or more of the optical ports 52 and 72, where the membrane can be doped with phenol red (phenolsulfonphthalein).

The bioreactor device further can include one or more chemical sensors 66, such as sensors capable of measuring oxygen tension, and thus determining oxygen concentration in the bioreactor chamber. Suitable chemical sensors include doped sol-gels and doped membranes in contact with the sample contained in the bioreactor chamber or preferably separated from the sample by a thin chemically permeable encapsulant. A preferred oxygen sensor is a ruthenium doped sol-gel coated glass slide encapsulated with silicone. By observing the chemical glass sensors 66, it is possible to determine oxygen tension, and thus oxygen concentration to control sample growth conditions and determine viability of the sample. A preferred pH chemical sensor is a phenol doped membrane. The chemical sensors provided in the bioreactor device can be read optically through the optical ports 52 and/or 72, e.g., by using a microscope in fluorescence mode or a spectrophotometer (see FIG. 5).

Referring to FIGS. 1A, 4, and 6A-6D, methods for testing mechanical properties of samples in the bioreactor chamber are shown. For controlled force or displacement loading of a sample, valve 44 is switched to B and valves 34 and 36 are opened (see FIG. 1A). A unidirectional or open septum in the fluid reservoir 40 is employed with a sufficient amount of air in the reservoir. FIG. 6A depicts functional steps implemented in the bioreactor hardware for controlled displacement testing (e.g., stress relaxation test) of the sample in the bioreactor chamber 16 (see FIG. 4). The desired displacement waveform of the membrane 74 (see FIG. 4) is discretized by a CPU 100 having the waveform stored in memory 102 into sampled displacement values that are provided to a control loop 104 which converts the desired displacement to the required pump rotation while simultaneously sampling the pressure applied to produce the membrane 74 displacement via a pressure sensor 65 and converting the pressure value to the value of applied force to the sample. The sampled displacement and force values are stored for analysis. A similar control process may be implemented to displace the membrane 74 up or down with an external plunger connected through the top optical port 52 (see FIG. 2A).

FIG. 6B depicts the functional processes for controlled force testing (e.g., creep test) of a sample. The desired force waveform to be applied to the sample through the membrane 74 is discretized by the CPU 100 into sampled force values that are provided to a control loop 110 which converts the force value to the required pressure necessary to achieve the given force value. A second feedback loop 112 samples the pressure above the membrane 74 using a pressure sensor 65 and drives the pump rotation in finite increments to cause the sampled pressure to equal the required pressure value while simultaneously converting the finite values of pump rotation into sampled displacement values of the membrane 74. The sampled force and displacement values are stored for analysis. For permeability testing of the sample, the valve 44 is switched to A, the valve 38 is closed, and the valves 32 and 36 are opened (see FIG. 1A). A unidirectional or open septum in the fluid reservoir 40 is employed with a sufficient amount of air in the reservoir. A similar control process may be implement to apply force through the membrane 74 with an external plunger connected through the top optical port 52 (see FIG. 2).

FIG. 6C depicts the control steps implemented in the bioreactor hardware to generate controlled fluid flow rates for permeability testing of a sample. The desired flow rate waveform is discretized by the CPU 100 into sampled flow rate values that are provided to a control loop 120 which converts flow rate to the required pump rotation while simultaneously sampling differential pressure across the bioreactor chamber 16 using pressure sensors 65 in chambers 18 and 20 (see FIG. 1A). The sampled pressure values and flow rates are stored for analysis.

FIG. 6D is a flowchart of the bioreactor method and diagram of the bioreactor electrical circuit for impedance testing of a sample within the bioreactor chamber. Static and oscillating electric fields are applied across the sample in chamber 16 using electrodes 63 and the current and voltage across the sample monitored with an external unit. For example, and external impedance analyzer may be connected to the electrodes 63 and used to determine the conductivity and capacitance of the sample, which are proportional to the density of the sample and cellularity. Such a method falls under the technique of dielectric spectroscopy.

The bioreactor device according to the subject invention can be used to make various measurements of system parameters and sample growth. For example, permeability and compressive modulus can be measured, where it can be observed that as permeability decreases, a sample (e.g., tissue) contained in the bioreactor chamber becomes more dense. Thus, by pumping fluid through the bioreactor chamber, differential pressure can be measured across the sample, which provides a measurement of permeability. One or more pressure sensors 65 can be arranged in the bioreactor device or fluid circuit, e.g., near the pump 42 shown or the sample chamber in FIG. 1. Various other measurements can be made through the previously described temperature, pH, and chemical sensors, where observations can be made through electronic output from the sensors and the one or more optical ports 52 and/or 72. The bioreactor device of the subject invention allows a sample (e.g., tissues or cells) to be imaged in real time. For example, the cells of a sample can be infected with reporter constructs that fluoresce under biologic conditions of interest, and microscopy is used to monitor the cells and the signal from reporter constructs in real time. Various known techniques and devices can be used to carry out spectroscopy and microscopy measurements in situ on samples contained in the bioreactor chamber.

The bioreactor device of the subject invention is capable of delivering different types of mechanical loadings to the tissue sample, such as fluid shear, hydrostatic pressure, and matrix compression, as described with reference to FIG. 1. During matrix compression, the multilevel arrangement of the bioreactor chamber is utilized such that the upper level of the bioreactor chamber, including a silicone sheet 74, exhibits downward displacement over the lower level of the bioreactor chamber (see FIG. 4). According to this arrangement, fluid (medium) is pumped only into the upper level of the bioreactor chamber. The bioreactor device and system also flexibly allows other mechanical loadings to be carried out, including fluid shear and hydrostatic pressure, without resulting in any changes to the structure or function of the bioreactor device, where such mechanical loadings can be carried out in situ.

Figure 5:
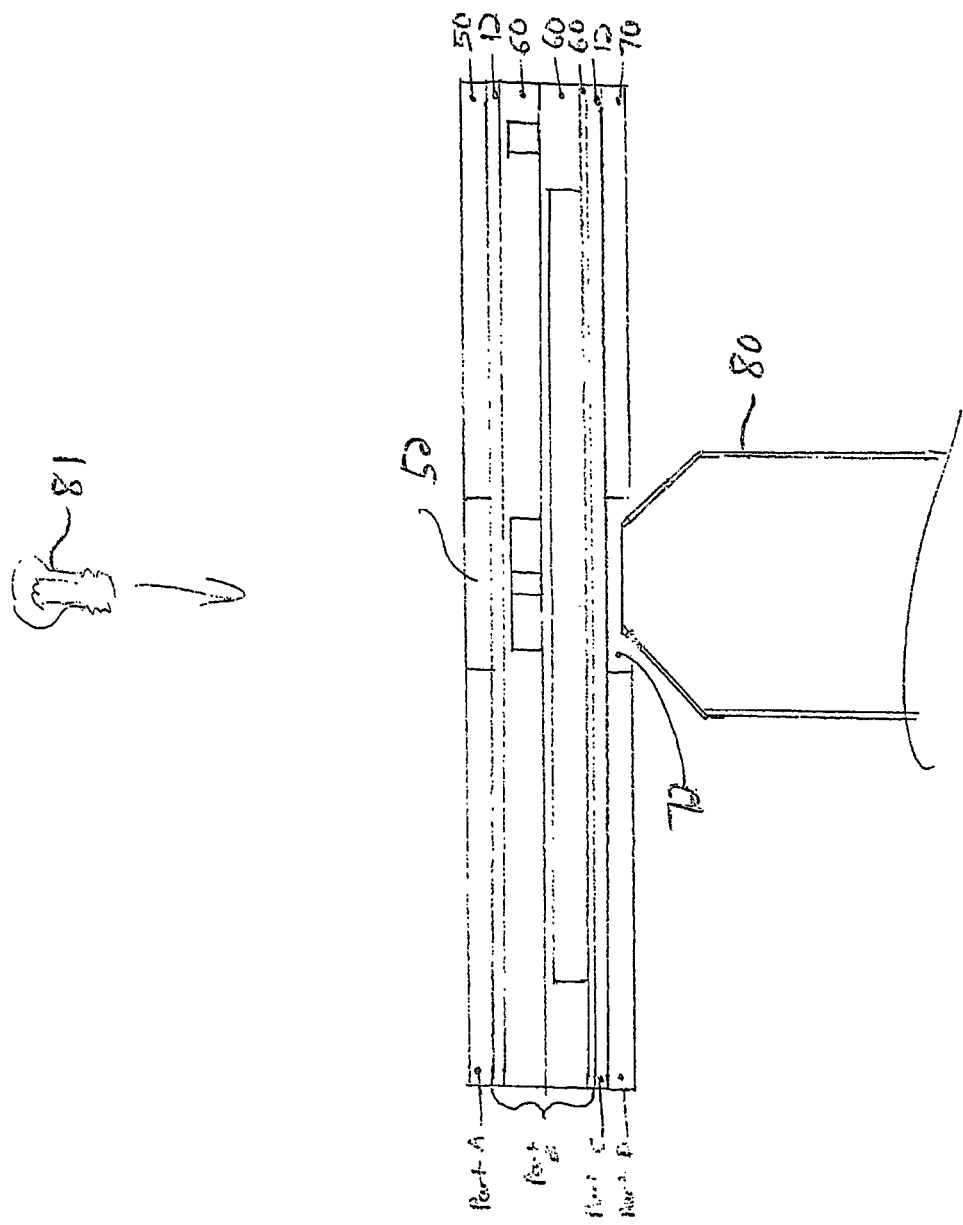
FIG. 5 is a cross-sectional side view of the bioreactor device of FIG. 3A during imaging of a sample.

Imaging can be provided in situ while mechanical stimulation is being delivered to a sample contained in the bioreactor chamber and while biofactors are being delivered to a sample contained in the bioreactor. Samples contained in the bioreactor subject to simultaneous mechanical stimulation and biofactor delivery can also be imaged in real time. As previously described, imaging can involve spectroscopy or microscopy, and can include monitoring various system parameters, e.g., through temperature, pH, and chemical sensors. An exemplary imaging technique is shown in FIG. 5, in which an objective lens 80 is arranged proximate the optical port 72, as illuminated by a light source 81. Other suitable imaging arrangements are within the scope of the subject invention.

Polymers useful in the bioreactor include olefin polymers, polyethylene, polypropylene, polyvinyl chloride, polytetrafluoroethylene, fluorinated ethylene propylene copolymer, polyvinyl acetate, polystyrene, poly(ethylene terephthalate), polyurethane, polyurea, silicone rubbers, polyamides, polycarbonates, polyaldehydes, natural rubbers, polyester copolymer, styrene-butadiene copolymers, alpha-hydroxyacids, polycaprolactone, polyanhydrides, polymethylmethacrylate, polypropylenefumarate, and combinations thereof. Useful polymer reactive chemistries include those based on acrylates, epoxy compounds, vinyl ethers and thiolene systems. Also useful in the bioreactor of the invention are hydrogels, which are elastic solids in the sense that there exists a remembered reference configuration to which the system returns even after being deformed for a very long time, including hydrogels of polyvinyl alcohols, polyethylene glycols, alginates, pluronics (PEO-PPO-PEO, i.e. PEO=poly (ethylene oxide), PPO=poly(propylene oxide)), and of biological materials such as collagen, fibrin and dextran gels.

In embodiments where one or more cells are grown in the bioreactor, the cells may be any cell or cell type, for instance a prokaryotic cell or a eukaryotic cell. For example, the cell may be a bacterium or other single-cell organism, a plant cell, an insect cell, a fungi cell or an animal cell. If the cell is a single-cell organism, then the cell may be, for example, a protozoan, a trypanosome, an amoeba, a yeast cell, algae, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a mammalian cell such as a primate cell, a bovine cell, a horse cell, a porcine cell, a goat cell, a dog cell, a cat cell, or a cell from a rodent such as a rat or a mouse. If the cell is from a multicellular organism, the cell may be from any part of the organism. For instance, if the cell is from an animal, the cell may be a cardiac cell, a fibroblast, a keratinocyte, a heptaocyte, a chondrocyte, a neural cell, a osteocyte, a muscle cell, a blood cell, an endothelial cell, an immune cell (e.g., a T-cell, a B-cell, a macrophage, a neutrophil, a basophil, a mast cell, an eosinophil), a stem cell, somatic stem cell, fibrocytes, vascular endothelial cells, liver cells, small intestine epithelial cells, epidermis keratinized cells, osteoblasts, bone marrow mesenchymal cells. etc. In some cases, the cell may be a genetically engineered cell. In certain embodiments, the cell may be a Chinese hamster ovarian ("CHO") cell or a 3T3 cell. In some embodiments, more than one cell type may be used simultaneously, for example, fibroblasts and hepatocytes. In certain embodiments, cell monolayers, tissue cultures or cellular constructs (e.g., cells located on a nonliving scaffold), and the like may also be used in the bioreactor. The precise environmental conditions necessary in the bioreactor for a specific cell type or types may be determined by those of ordinary skill in the art. The cells may be transformed expressing or over-expressing a proteins, peptides, and/or nucleic acids. The cells may be cells useful for growing on scaffolds for tissue engineering (immature tooth pulp, cartilage, cardiac cells, liver cells, kidney cells, stem cells, and the like) or providing cells for cell replacement (blood cells, skin cells, and the like).

In the culturing of cells, generally a culture solution (e.g., D-MEM medium, MEM medium, HamF12 medium, or HamF10 medium) at a concentration of about 10,000 to 150,000 cells/ml, or higher, is used. The culture condition of cells may be appropriately selected depending upon the cells to be cultured.

In some instances, the cells may produce chemical or biological compounds of therapeutic and/or diagnostic interest, for instance, in nanogram, microgram, milligram or gram or higher quantities. For example, the cells may be able to produce products such as monoclonal antibodies, proteins such as recombinant proteins, amino acids, hormones, vitamins, drug or pharmaceuticals, other therapeutic molecules, artificial chemicals, polymers, tracers such as GFP ("green fluorescent protein") or luciferase, etc. In one set of embodiments, the cells may be used for drug discovery and/or drug developmental purposes. For instance, the cells may be exposed to an agent suspected of interacting with the cells. Non-limiting examples of such agents include a carcinogenic or mutagenic compound, a synthetic compound, a hormone or hormone analog, a vitamin, a tracer, a drug or a pharmaceutical, a virus, a prion, a bacteria, etc. For example, in one embodiment, the invention may be used in automating cell culture to enable high-throughput processing of monoclonal antibodies and/or other compounds of interest. In another embodiment, the invention may be used to screen cells, cell types, cell growth conditions, or the like, for example, to determine self viability, self production rates, etc. In some cases, the invention may be used in high through put screening techniques. For example, the invention may be used to assess the effect of one or more selected compounds on cell growth, normal or abnormal biological function of a cell or cell type, expression of a protein or other agent produced by the cell, or the like. The invention may also be used to investigate the effects of various environmental factors on cell growth, cell biological function, production of a cell product, etc.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications, and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A bioreactor device, comprising:
   at least one millifluidic bioreactor chamber for containing a sample greater than about 10 µL in volume, in local medium volume of less than approximately 1 mL, the bioreactor chamber configured to deliver a plurality of types of mechanical and electrical stimulation to a sample contained in the bioreactor chamber;
   plates on opposing sides of the bioreactor chamber for containing the sample there between;
   the bioreactor chamber including at least one inlet flow channel and at least one outlet flow channel, the inlet and outlet flow channels configured for periodic and/or continuous perfusion of the medium through the bioreactor chamber;
   an optical port for obtaining measurements of the sample contained in the bioreactor chamber; and
   a fluid circuit in connection with the bioreactor chamber for controlling perfusion of the medium to the bioreactor chamber, wherein the fluid circuit includes a reservoir having at least one septum that divides the reservoir into multiple compartments and regulates fluid flow and fluid mixing between the multiple compartments.

2. The bioreactor device of claim 1, wherein the sample is contained in local medium volume of less than approximately 200 µL.

3. The bioreactor device of claim 1, wherein the plurality of types of mechanical stimulation include at least one of fluid shear, reciprocating fluid shear, hydrostatic pressure, matrix compression, and clinorotation.

4. The bioreactor device of claim 1, wherein reciprocating fluid shear stimulation is generated with a positive pressure head in both directions using only one pump.

5. The bioreactor device of claim 1, wherein the bioreactor chamber includes at least one filter to contain the sample.

6. The bioreactor device of claim 1, wherein the bioreactor chamber includes a plurality of levels.

7. The bioreactor device of claim 1, wherein the bioreactor chamber includes at least an upper level, and a lower level for containing the sample.

8. The bioreactor device of claim 7, wherein the lower level of the bioreactor chamber is compressed when medium is perfused into the upper level of the bioreactor chamber.

9. The bioreactor device of claim 8, wherein force applied by the upper level onto the lower level is a function of fluid pressure in the upper level and displacement of the lower level is a function of the amount of fluid pumped into the upper level.

10. The bioreactor device of claim 1, further including ISFET sensors for measuring ionic species in the medium.

11. The bioreactor device of claim 1, further including at least one sensor for measuring oxygen tension.

12. The bioreactor device of claim 1, further including doped sol-gel coated glass surfaces for detecting substances using fluorescence quenching.

13. The bioreactor device of claim 1, wherein the sample includes a plurality of cells.

14. A system for growing a sample in a bioreactor device, comprising:
   at least one bioreactor chamber including:
      (i) at least one level for containing the sample in less than about 1 mL of local medium, the bioreactor chamber configured to receive a plurality of types of mechanical and electrical stimulation while the sample is contained in the bioreactor chamber;
      (ii) at least one inlet flow channel and at least one outlet flow channel, the inlet and outlet flow channels configured for periodic and/or continuous perfusion of the medium through the bioreactor chamber;

(iii) an optical port for obtaining measurements and images of the sample contained in the bioreactor chamber; and (iv) embedded sensors for obtaining measurements of the sample contained in the bioreactor chamber;

a fluid circuit for controlling delivery of the medium to and from the bioreactor chamber, wherein the fluid circuit includes a reservoir for containing medium and/or biofactors, the reservoir having at least one septum that divides the reservoir into multiple compartments and regulates fluid flow and fluid mixing between the multiple compartments by permitting bidirectional fluid flow and diffusion between the multiple compartments, restricting fluid flow and diffusion to one direction, and inhibiting fluid flow and diffusion between compartments; and a pre-chamber for biofactor delivery to the bioreactor chamber.

15. The system of claim 14, wherein the sample is contained in local medium volume of less than approximately 200 μL.

16. A method for growing a sample in a bioreactor device, comprising the steps of:

inserting the sample in a bioreactor chamber containing less than about 1 mL of local medium, the bioreactor chamber configured to receive a plurality of types of mechanical stimulation while the sample is contained in the bioreactor chamber;

connecting the bioreactor chamber to a fluid circuit, wherein the fluid circuit includes a reservoir containing medium and/or biofactors, the reservoir having at least one septum that divides the reservoir into multiple compartments and regulates fluid flow and fluid mixing between the multiple compartments by permitting bidirectional fluid flow and diffusion between the multiple compartments, restricting fluid flow and diffusion to one direction, and inhibiting fluid flow and diffusion between compartments;

periodically and/or continuously perfusing the medium through the bioreactor chamber through the at least one flow channel;

delivering biofactors to the bioreactor chamber;

stimulating the sample contained in the bioreactor chamber with at least one of mechanical and electrical forces and biofactors; and obtaining measurements of the sample contained in the bioreactor chamber while simultaneously stimulating the sample with mechanical and electrical forces and biofactors, wherein the ratio of local medium volume to sample volume is two or less.

17. The method of claim 16, wherein the sample is contained in local medium volume of less than approximately 200 μL.

18. The bioreactor device of claim 1, wherein the bioreactor chamber, the inlet flow channel, the outlet flow channel, and the fluid circuit are configured for periodically and/or continuously perfusing the medium through the bioreactor chamber so as to maintain a ratio of local medium volume to sample volume of two or less.

19. The bioreactor device of claim 1, wherein the bioreactive chamber comprises an upper level and multiple lower levels, the upper level and multiple lower levels each individually coupled to discrete fluid circuits, wherein the multiple lower levels are configured for production and growth of multiphasic tissues.

20. The bioreactor device of claim 1, wherein the bioreactive chamber comprises an upper level and multiple lower levels, the upper level configured for applying matrix compression.

21. The system of claim 8, wherein the fluid circuit further comprises a (a) first fluid pathway extending from the at least one outlet flow channel of the bioreactor chamber to the reservoir, and then to the at least one inlet flow channel of the bioreactor chamber, and (b) a second fluid pathway extending from the at least one outlet flow channel of the bioreactor chamber to the at least one inlet flow channel of the bioreactor chamber.

22. The system of claim 21, wherein the fluid circuit further comprises a first and second valve in the first fluid pathway and a third valve in the second fluid pathway, wherein opening and closing of the first, second, and third valves controls flow of medium through the first fluid pathway and/or second fluid pathway.

23. The system of claim 1, wherein the bioreactor chamber comprises an upper level and a lower level, the lower level for containing the sample and the upper level for providing matrix compression to the sample in the lower level.

24. The system of claim 23, wherein the bioreactor chamber further comprises an inlet for fluid flow to the upper level, wherein fluid flow to the upper level provides matrix compression.

* * * * *